United States Patent [19]

Prince et al.

[11] Patent Number: 5,069,792
[45] Date of Patent: Dec. 3, 1991

[54] ADAPTIVE FILTER FLOW CONTROL SYSTEM AND METHOD

[75] Inventors: Paul R. Prince, San Juan Capistrano; William D. Callaway, Huntington Beach, both of Calif.

[73] Assignee: Baxter International Inc., Deerfield, Ill.

[21] Appl. No.: 551,598

[22] Filed: Jul. 10, 1990

[51] Int. Cl.$^5$ ............................................. B01C 13/00
[52] U.S. Cl. ..................................... 210/627; 210/651; 210/90
[58] Field of Search ................. 210/651, 929, 637, 85, 210/87, 90, 433.1; 604/4-6

[56] References Cited

U.S. PATENT DOCUMENTS

| | | |
|---|---|---|
| 3,949,734 | 4/1976 | Edwards et al. |
| 4,086,924 | 5/1978 | Latham, Jr. |
| 4,285,464 | 8/1981 | Latham, Jr. |
| 4,401,431 | 8/1983 | Arp |
| 4,447,191 | 5/1987 | Bilstad et al. |
| 4,468,219 | 8/1987 | George et al. |
| 4,481,827 | 11/1984 | Bilstad et al. |
| 4,657,529 | 4/1987 | Prince et al. |
| 4,879,040 | 11/1989 | Prince et al. ......................... 210/651 |

Primary Examiner—Frank Sever
Attorney, Agent, or Firm—June M. Bostich; Bruce M. Canter

[57] ABSTRACT

An adaptive filter concentrate flow control system and method includes a filter system, a pumping system driving feed fluid, concentrate and filtrate flowing through the filter system and a flow control system controlling the pumping system to maintain optimum filtrate flow rates or minimum feed flow rates along a control surface in a three dimensional transmembrane pressure—feed fluid rate—filtrate flow rate space. Actual sensed operating point data is used to locate the control surface so as to assure an optimized filtrate flow rate or minimized feed flow rate at which reversible blocking of the membrane has begun to occur without irreversible blocking or plugging. The system is advantageously employed to control and maximize the flow of plasma in a plasmapheresis system or to minimize the rate at which blood is withdrawn from a donor and introduced into the system while achieving a fixed rate of plasma flow.

35 Claims, 6 Drawing Sheets

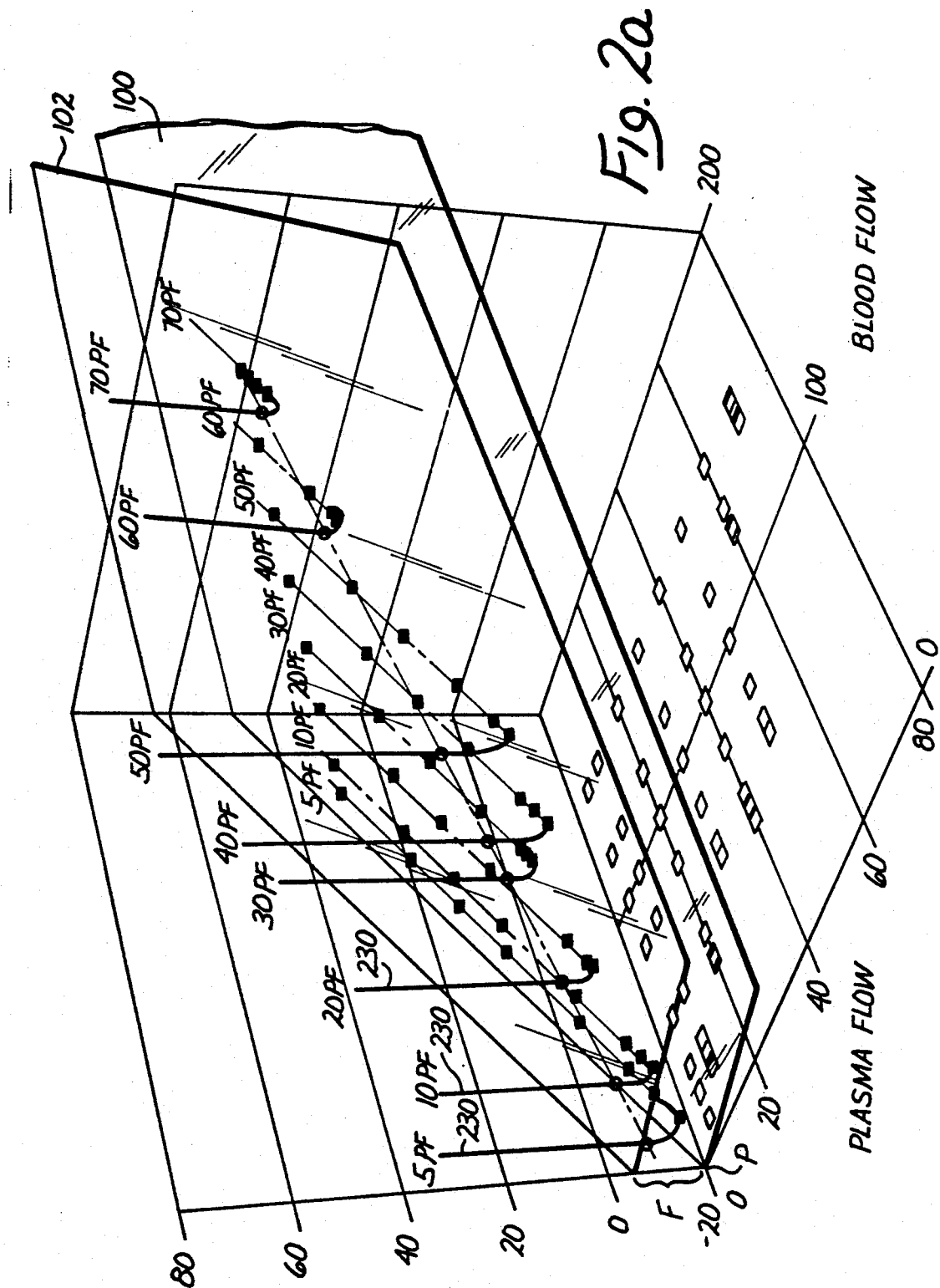

ADAPTIVE FILTER FLOW CONTROL SYSTEM AND METHOD

BACKGROUND OF THE INVENTION

1. Field of the Invention

This invention relates to the optimization of concentrate flow in a filter system and more particularly to a system using actual sensed operating curve data to optimize plasma flow in a plasmapheresis system.

2. Discussion of the Prior Art

Conventional filtering systems involve a tripartite fluid flow relative to a porous membrane. Feed fluid which is to be filtered is presented to a first side of the membrane and flows across the first side of the membrane along a longitudinal axis of the filter system. Filtrate fluid passes through the membrane and is withdrawn from the second side of the membrane, opposite the first side. Components of the feed fluid which pass along the membrane without passing therethrough are drawn off as a retentate or concentrate fluid.

In a typical filtering application such as a plasmapheresis system wherein plasma is separated from whole blood to form a packed cell concentrate, it is desirable to maximize the percentage or absolute flow rate of the filtrate. For moderate filtrate flow rates and fixed membrane area, the filtrate flow rate is approximately proportional to transmembrane pressure (TMP). However, as the filtrate flow rate increases a reversible blocking effect causes transmembrane pressure to increase more rapidly relative to filtrate flow. The blocking effect is reversible in the sense that if the filtrate flow is decreased after blocking has occurred there is no plugging of the filter pores and the original substantially linear TMP-filtrate flow relationship is reestablished.

However, if the filtrate flow (and TMP) become sufficiently high, red cells, platelets or other particulate matter lodge permanently in the membrane pores and begin to irreversibly plug the filter. The plugging decreases the effective area of the membrane and if continued over a period of time will cause the filtrate flow rate to decrease while the TMP remains constant or even increases, or will cause an increase in TMP if the filtrate flow rate is maintained. If the filtrate flow rate is decreased the filter membrane remains partially plugged and the effective area of the membrane is permanently decreases wherein the original TMP-filtrate flow relationship is changed undesirably.

One filter flow control system is partially described in Lysaght, M. J.; Schmidt, B.; Samtleen, W.: and Gurland, H. J. "Transport Considerations in Flat Sheet Microporous Membrane Plasmapheresis," *Plasma Therapy Transfusion Technology*, Vol. 4, No. 4 (1983) pp. 373–85. The described system uses a pumping system with pumps driving the feed fluid (blood) and filtrate (plasma). The controls system senses pump flow rates in the feed fluid and filtrate paths and senses pressure in all three filter fluid paths. A clamp also controls the flow of feed fluid over the membrane surface. The sensed information is used by an undisclosed control algorithm to control the filtrate flow and clamp to keep TMP constant and to maintain a desired inlet to outlet pressure differential.

Some systems use a capillary separator in place of a flat membrane device. The capillary separator uses hollow fibers with thin, porous walls. The walls of the fibers are essentially porous membranes and function in a manner similar to a flat membrane. A system using a capillary separator is described in Buchholz, D. H.; Porten, J.; Anderson, M.; Helphigstine, C.: Lin, A.; Smith, J.; Path, M.; McCullough, J.; and Snyder, E.; "Plasma Separation Using the Fenwal COS-10 Capillary Plasma Separator," *Plasmapheresis*, edited by Y. Nose, P. S. Malcesky, J. W. Smith and R. S. Krakauer, Raven Press, New York (1983).

SUMMARY OF THE INVENTION

An adaptive filter fluid flow control system in accordance with the invention includes a filter system having a porous membrane filter, a flow regulating system having pumps coupled to drive feed fluid, concentrate and filtrate through the filter system, a pressure sensor coupled to detect and indicate transmembrane pressure and a filter fluid control system coupled to control the pumping system to optimize filtrate flow rated in response to transmembrane pressure (TMP). In an alternative embodiment the pumping system can be controlled to minimize the rate at which feed must be fed into the filter to achieve a predetermined fixed rate of filtrate flow.

The filter system is characterized by an initial linear increase in the pressure differential across the filter for any fixed feed flow rate as the amount of filtrate pushed through the filter increases, but reaches a point at which further increases in filtrate flow rate cause reversible blocking of the filter so that the pressure drop across the filter rises in a non-linear fashion. A corresponding initial linear decrease in the pressure occurs for any fixed filtrate flow rate as the amount of feed is decreased. At any point in the regime of linear pressure decrease the blocking of the filter can be substantially reversed by reducing the rate of filtrate flow in the first embodiment and increasing feed flow in the second embodiment. However, further increases in the rate of filtrate flow or decreases in feed flow result in irreversible blocking (i.e. plugging) of the filter and consequent rapid increase in the pressure differential across the filter.

Therefore, the optimal rate of filtrate flow is obtained by selecting as an operating point a rate of filtrate flow slightly above the initial linear region of pressure increase in the region of reversible blocking, but lower than the rate at which irreversible blocking or plugging sets in. Accordingly, the minimum rate of feed flow required to obtain a required output of filtrate flow is obtained by selecting as the optimum operating point a rate of feed flow slightly below the initial linear region of reversible blocking. At this latter point the rate of feed flow required to maintain the optimal operating point is minimized.

The filter fluid control system of the invention is designed to hold the operating point of the system at or near the optimal operating point for any given feed flow or for any given filter flow rate. The filter fluid control system therefore detects data for at least one actual system TMP-filtrate flow rate operation point, in a three dimensional coordinate system having pressure versus blood flow rate as one set of coordinates and pressure versus plasma flow rate as the second set of coordinates; extrapolates the actual operating point data to form a prediction plane and then translates the prediction plane upwards along the vertical pressure axis a fixed distance and adjusts it, if needed to meet the requirements of the system, to derive a control surface. Usually, however, the control surface is a plane approximately parallel to the prediction plane and offset vertically by an empirically derived amount. At all possible actual operating points located upon the control plane for various combination of blood flow and plasma flow, the filter is in the condition of reversible blocking. The control system is designed to continuously adjust the relative speeds of the pumps to maintain the actual operating point upon the control surface.

Moreover, in the three-dimensional coordinate space the location of all actual steady-state operating points (sensed system pressures) for any given input of feed flow rate lie upon a curve positioned along a plane orthogonal to the plane of constant-pressure and parallel to the plasma flow axis characterized by constant blood flow rate and variable plasma flow rates. At points representing low filtrate flow rates the constant feed flow curve is linear and lies along the prediction plane but at increasing values of filtrate flow the curve becomes non-linear (representing reversible blocking of the filter) and then rapid (representing irreversible blocking or plugging of the filter). Therefore the constant blood flow fluid characteristics curve pierces the above described control plane at a point that represents an optimal filtrate flow rate for any desired fixed input of feed to the filter.

The system can also be operated to maintain the filtrate production rate at a constant and minimize the rate of feed flow. This mode of operation is particularly desirable when performing certain therapeutic plasma processing procedures or at any time during blood processing when it is desirable to maintain blood flow at a minimum to cut down on the amount of anticoagulant returned to the subject and provide a specified plasma flow rate. When the system is operated under conditions of constant filtrate flow the fluid characteristics curve is located upon a plane orthogonal to a plane of constant pressure and parallel to the feed flow axis. At high feed flow rates the curve is linear and lies along the prediction plane, but at decreasing feed flow rates the system pressure rises non-linearly and rapidly so that the curve pierces the control plane at an point representing an optimum low feed flow rate for the desired constant filtrate flow rate.

Therefore a filter system can be operated so as to maximize the output of filtrate or so as to minimize the input of feed without the constant risk of damage to the filter or to red cells when the filter is used in plasmapheresis.

The filter system has particular advantage when used in a plasmapheresis system wherein the feed fluid is whole blood, the concentrate is packed cells and the filtrate is plasma. In a plasmapheresis system the blood flow rate is often controlled to maximize the rate at which plasma can be safely removed from the donor, depending upon the donor's maximum rate of blood supply. However, in some cases the need arises to minimize the flow rate of blood withdrawn from the donor or patient while a fixed amount of plasma is obtained. The filter system of the invention can be used to maintain the filtering operation at the operating point representing substantially the lowest possible blood rate required to attain a fixed rate of plasma. Because the sum of the concentrate and filtrate flow rates must match the feed flow rate, plasma flow rate can be controlled by actively controlling the speed of peristaltic pumps which pump the blood and the packed concentrate fluids.

BRIEF DESCRIPTION OF THE DRAWINGS

A better understanding of the invention may be had from a consideration of the following Detailed Description taken in conjunction with the accompanying drawings in which:

FIG. 2a is a graphical illustration of a three dimensional coordinate space having located therein constant plasma flow fluid characteristic curves that are useful in understanding the operation of the filter system shown in FIG. 1;

DETAILED DESCRIPTION OF THE PREFERRED EMBODIMENT

Figure 1:
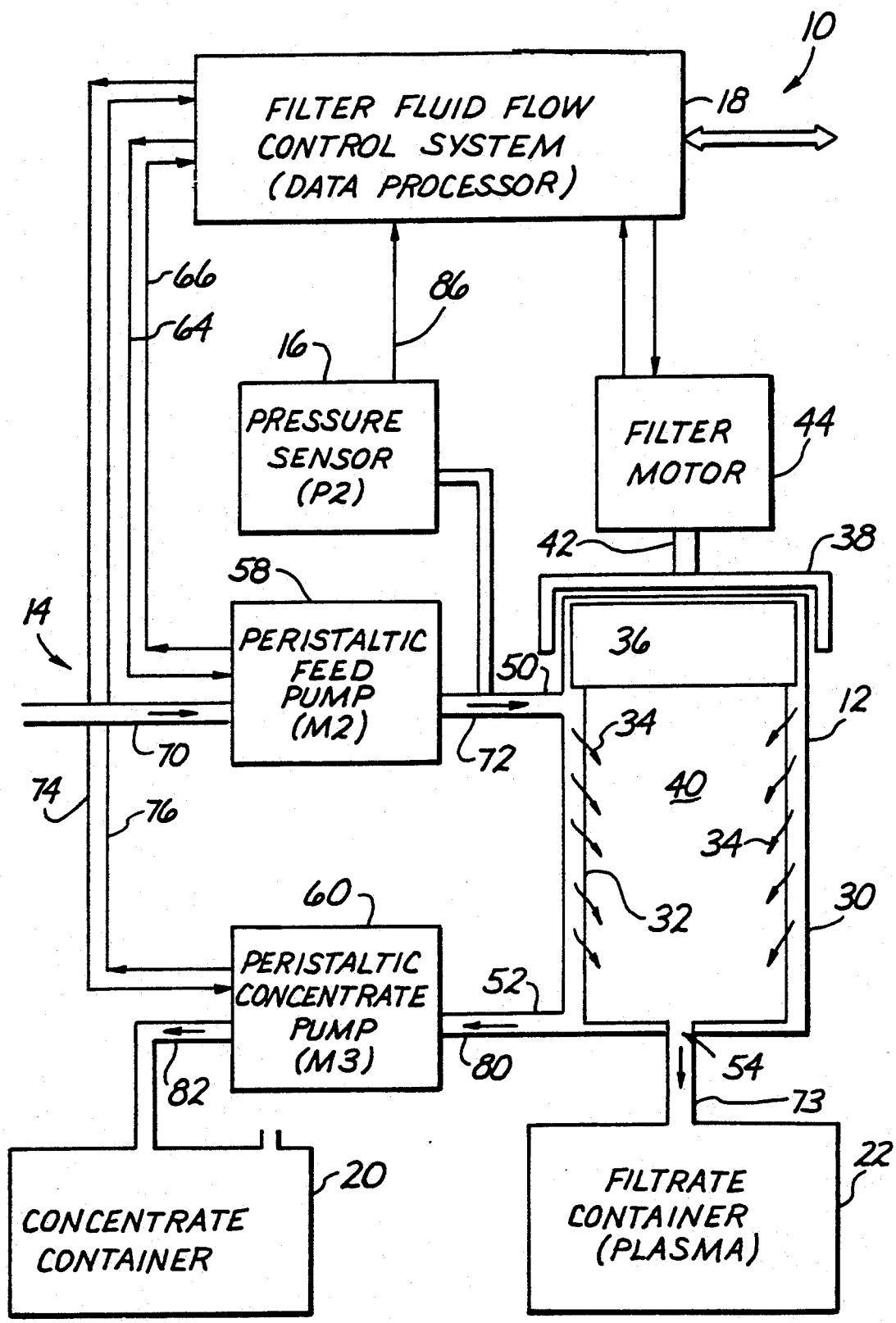
FIG. 1 is a schematic and block diagram representation of an adaptive filter fluid flow control system in accordance with the invention.

Referring now to FIG. 1, there is shown an adaptive filter fluid flow control system 10 in accordance with the invention including a filter system 12, a pumping system 14, a P2 pressure sensor 16, a filter fluid flow control system 18, a concentrate container 20 and a filtrate container 22. While the filter system 10 may be utilized for other appropriate filtering applications, it is particularly useful for filtering plasma from whole blood in a plasmapheresis system in which such a filter system 10 might be utilized is found in a co-pending, commonly assigned patent application Ser. No. 06/626,034 filed June 29, 1984 by Paul Prince et al for "Blood Extraction and Reinfusion Flow Control System and Method", now abandoned and superseded by U.S. Pat. No. 4,657,529.

The filter system 12 may alternatively be a stationary flat membrane or capillary separator type of system but is preferably of the vortex enhanced shear flow separator type having a generally cylindrical housing 30 enclosing a cylindrically shaped rotating filter membrane 32 having pores through which a filtrate such as blood plasma may flow as indicated by arrow 34.

Two magnetic pole pieces 36, 38 provide a magnetic coupling through the hermetically sealed filter housing 30 to cause a rotator 40 supporting the filter membrane 32 and magnetic coupling 36 to rotate in response to fa filter motor 44 and shaft 42. Filter motor 44 is conventionally driven at a controlled velocity in response to commands from the filter fluid flow control system 18. Filter motor 44 includes position feedback sensing devices in the form of Hall effect devices which return to filter fluid flow control system 18 twelve uniformly distributed pulses for each rotation of filter motor 44.

The present invention is not concerned with the specific configuration of the filter system 12. The filter system 12 has thus been represented in a somewhat schematic and idealized form. However, a more complete description of a preferred configuration for the filter system 12 can be found in a commonly assigned patent application Ser. No. 591,925 filed Mar. 21, 1984 for "Method and Apparatus for Separation of Matter from Suspension", by Donald W. Schoendorfer.

In operation, the filter system 12 receives an anticoagulant protected whole blood feed fluid at an inlet 50. The feed fluid surrounds the cylindrical, rotation membrane 32 and flows longitudinally downward toward a concentrate or retentate which is packed cells for the presently disclosed application of use in a plasmapheresis system. As the feed fluid flows longitudinally downward from the inlet 50 to the outlet 52 a filtrate component thereof, which is plasma in the present instance, passes through pores in the filter membrane 32 as indicated by arrows 34 to exit the filter system 12 through a filtrate outlet 54 which is coupled to the filtrate container 22. The filtrate container 22 is schematically illustrated as being vented to the atmosphere. However, in the preferred embodiment the container 22 is actually a flexible bottle or container which maintains the filtrate fluid at atmospheric pressure while isolating the fluid from atmospheric contamination.

The pumping system 14 includes a peristaltic feed pump 58 and a peristaltic concentrate pump 60. The peristaltic feed pump 58 includes a drive motor designated M2 which is coupled in a conventional manner to received velocity commands from filter fluid flow control system 18 over a control path 64. Like the filter motor 44 and motor M2 driving peristaltic feed pump 58 includes conventional Hall effect position sensor devices which provide to filter fluid flow control system 18 over a feedback path 66 rotational position indicating pulses with 12 pulses distributed over each cycle of rotation of the motor M2. Peristaltic feed pump 58 receives feed fluid through a conduit 70 from a suitable feed fluid source such as a donor subject in the particularly disclosed application and pumps the received feed fluid with a controlled flow velocity to the inlet 50 of filter system 12 through a conduit 72.

The peristaltic concentrate pump 60 is coupled in a conventional manner to receive velocity control signals over a control path 74 from filter fluid flow control system 18. Peristaltic concentrate pump 60 includes a drive motor M3 which receives the velocity control commands and has Hall effect position feedback sensing devices. The Hall effect devices provide to filter fluid control system 18 position feedback signals in the form of 12 pulses uniformly distributed over each rotation of the motor M3. The feedback pulses are communicated to the filter fluid flow control system 18 over a feedback path 76.

Peristaltic concentrate pump 60 receives retentate fluid from outlet 52 over a conduit 80 and pumps the retentate fluid at a controlled flow rate over a conduit 82 to the concentrate container 20. As with the filtrate container 22, the concentrate container 20 is shown having a vent to atmospheric pressure. However, it should be kept in mind that in the present application the concentrate within concentrate container 20 must be protected from atmospheric contamination as by using a filtration type of vent, or a flexible bag as the container.

It can readily be seen that once the filter system 12 is primed with fluid, the flow of feed fluid through inlet 50 must equal the flow of concentrate fluid through outlet 52 plus the flow of filtrate fluid through outlet 54. Consequently, by controlling the flow of concentrate fluid through peristaltic concentrate pump 60 relative to the flow of feed fluid through outlet 54 is inherently controlled even though no pump is disposed along the filtrate fluid path to directly control the flow of filtrate fluid. It is thus apparent that references to control of the filtrate fluid made in this disclosure can include indirect control over filtrate fluid flow by controlling the feed fluid flow and concentrate fluid flow as well as direct control over filtrate fluid flow.

It is further noted that in general any relative control of the fluid rates through feed pump 58 and concentrate pump 60 can be utilized to control the filtrate fluid flow rate, their difference equalling the filtrate flow rate for incompressible fluids. However, for the present application of a plasmapheresis system, it has been found desirable to control the feed pump 58 independently of the filter system 12 to optimize or in some cases to minimize the extraction of feed fluid from a subject donor serving as the source of feed fluid. The concentrate pump 60 is then controlled relative to the flow rate through the feed pump 58 to produce a system controlled filtrate flow rate through outlet 54. Alternatively, pump 60 could be positioned to control filtrate fluid flow through outlet 54 directly as suggested by dashed line 56. The remaining discussion assumes that pump 60 is positioned along the concentrate fluid flow path between conduits 80 and 82.

P2 pressure sensor 16 is coupled to sense pressure along the conduit 72 between the peristaltic feed pump 58 and the inlet 50 of filter system 12. Pressure sensor 16 responds to the sensed pressure by generating indications thereof which are communicated over a pressure feedback path 86 to the control system 18. Because pressure sensor 16 is coupled to a path which is in direct flow relationship with an inlet side of the membrane 32 and because the filtrate which is in direct flow relationship with an outlet side of the membrane 32 and filtrate conduit 73, and the filtrate container 22 is maintained at a constant, atmospheric pressure, the pressure sensed by sensor 16 includes the following pressure components: (1) hydrodynamic pressure loss, proportional to blood flow rate, in the conduit 72 between the sensor point and the inlet 50 and flow of blood through the gap (P blood flow), and in conduit 73 between outlet 54 and the filtrate container 22 (P plasma flow); (2) pressure head of filtrate that is dependent upon the particular relative elevations of the conduit 72 and the filtrate container 22 (P gravity); (3) atmospheric pressure at filtrate container 22; (4) centrifugally induced pressures resulting from rotation of the rotor 40 (P spin); as well as (5) hydrodynamic pressure loss as plasma flows through the filter device 30 (TMP).

The structure of the filter fluid flow control system 18 is not disclosed in detail. However, it may be implemented as a conventional microprocessor based control system having conventional analog to digital converters and digital to analog converters coupling the microprocessor to the motors and feedback devices of the adaptive filter system 10. Concentrate container 20 temporarily stores concentrate until full, wherein the plasmapheresis system pauses in the operation of filter 30 in order to return the concentrate to the fluid feed source. A combination of one filtration episode and one concentrate return comprises a filtration cycle.

In the present example each filtration operation or session begins with an initializing interval during which the feed pump 58 is operated at a constant and relatively low feed fluid flow rate of 60 milliliters per minute. This flow rate is selected to be well within the supply rate capacity for the feed fluid, and may be reduced to 30 ml/min, for example, if the blood flow capacity of the donor is low. During this initializing interval the filter system 12 is primed with fluid, and once stable operation is obtained, initializing measurements are taken. These measurements include the sensing and storing of pressure P2 at one or more relatively low filtrate flow rates. For example, pressure data can be acquired at a low filtrate flow rate of zero milliliters per minute and at 20 milliliters per minute.

Figure 2:
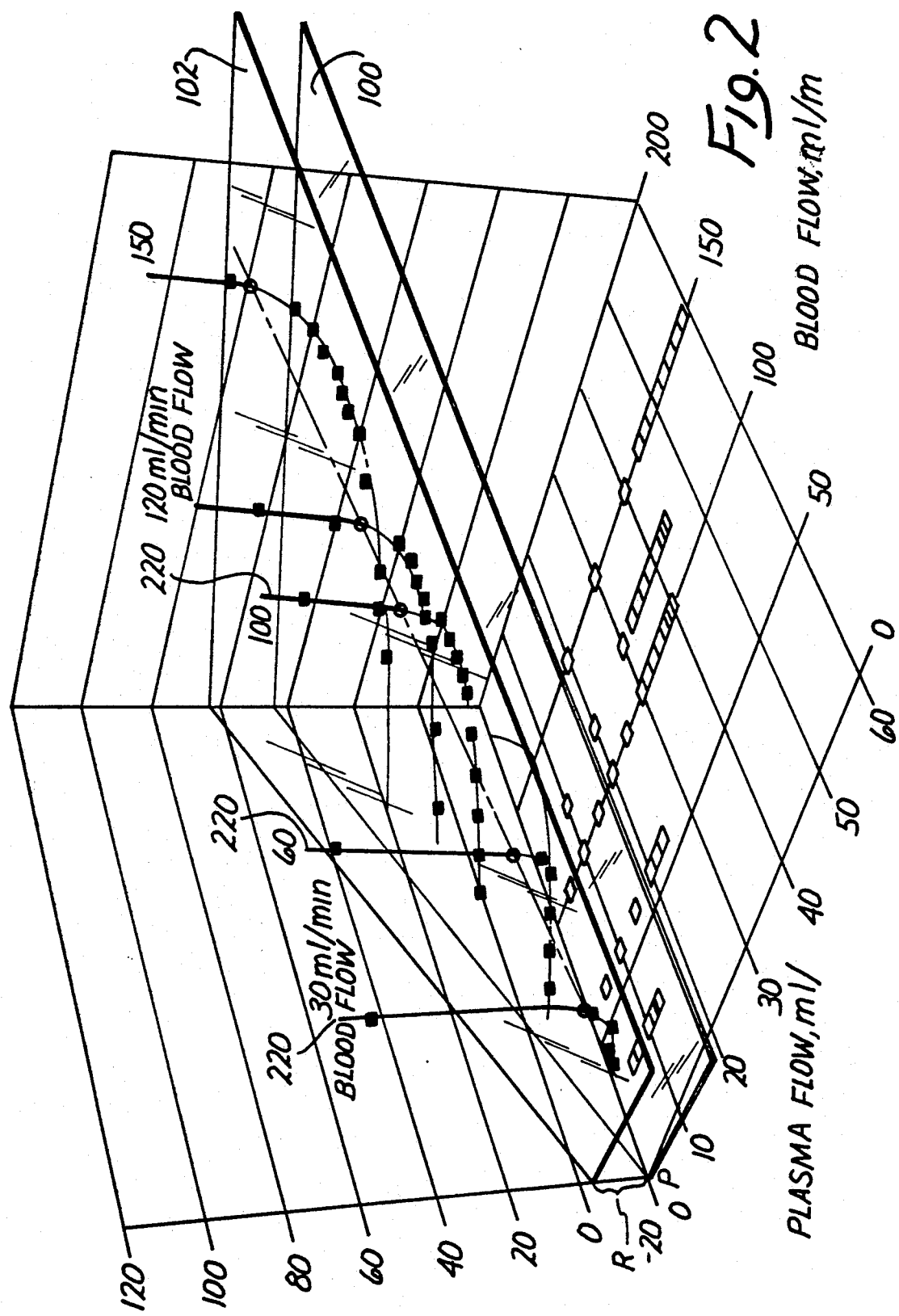
FIG. 2 is a graphical illustration of a three dimensional coordinate space having located therein constant blood flow fluid characteristic curves that are useful in understanding the operation of the filter system shown in FIG. 1.

A three-dimensional coordinate space having plotted thereon a plane and curves illustrating the method of controlling filtrate flow through a filter system in accordance with the present invention are shown in FIG. 2 to which reference is now made. It should be noted that the vertical axis of FIG. 2 indicates the pressure measured at pressure sensor P2 less the pressure component resulting from centrifugally induced pressures resulting from rotation of the rotor 40 (P spin). Point Q is determined by measuring actual pressure at a calibration blood flow rate located on the linear portion of the corresponding constant blood flow fluid characteristics curve 220 at a blood flow located in the linear portion of the curve, for example at 60 ml/min blood flow. Point P, the intersection of the prediction plane 100 with the vertical zero flow axis, is derived from the values of the pressure at point Q according to the following equation:

P(prediction)=Q−blood flow slope×calibration blood flow−plasma flow slope x calibration plasma flow The blood flow slope and the plasma flow slope depend upon the physical characteristics of the filter, such as surface area, pore size, and the composition of the filter, and can be empirically determined by taking pressure readings at two blood flows with low plasma flow (such as 10 ml/min) and at two plasma flow rates with sufficient blood flow (such as 60 ml/min). And for a spinning filter of the type illustrated in the preferred embodiment, the size of the gap between the filter and housing is also a determining factor. For example, the spinning nylon filter used to derive the control plane 102 illustrated in FIG. 2 with an average pore diameter of 0.6 micrometers and a surface area of about 40 square centimeters and a gap size of about 0.5 mm has a blood flow slope of 8 mm Hg per 30 ml per minute blood flow and a plasma flow slope of 12 mm Hg per 20 ml. per minute of plasma flow.

Point Q, the sensed pressure at a blood flow rate of 60 ml per minute and a 20 ml per minute plasma flow has a spin-corrected sensed pressure value of −12 mm Hg and point P(prediction) has a calculated pressure value of −28 mm Hg. P(control) is offset positively from P (prediction) by an empirically derived offset value of 12 mm Hg to assure that all points on the control plane 102 are located in the region of reversible filter blocking. Control plane 102 has a zero flow intercept at point P(control) of −8 mm Hg and has the above described blood flow and plasma flow slopes.

The amount of the pressure offset used to move the prediction plane 100 out of the region of linear pressure increase and into the region of reversible blocking will vary significantly depending upon the particular type of filter, length of tubings, and the like, and with the type of fluid filtered. Although the pressure offset is positive in the example illustrated in FIG. 2, in another type of system it might be negative.

In a plasmapheresis system, the pressure at P2 might typically be comprised of 100 mm Hg from centrifugal force induced pressure in the spinning membrane filter at 3600 rpm, for example, −28 mm Hg from the pressure head resulting from elevational differences between the pressure sensor and the filtrate container 22, and 8 mm Hg/30 blood flow hydrodynamic pressure. The transmembrane pressure is thus the pressure sensed at P2 less these offsets (P plasma flow is grouped with TMP). These flow rate related pressure changes tend to vary linearly with flow rate as sensed at pressure sensor P2 and are included in the slopes of the prediction plane 100. The plasma flow slope of the control plane 102 can be considered to represent changes in actual TMP.

Actual sensed pressures at constant blood flow rate lie along a fluid characteristic curve 220 which can be visualized as lying along a plane (not shown) orthogonal to the control plane 102 and parallel to the plasma flow axis in the pressure versus plasma flow coordinate system. A fluid characteristic curve 220 exists for each blood flow rate and lies along a series of such imaginary parallel planes. As can be seen in FIG. 2, at lower plasma flow rates the curve 220 is linear and corresponds to those values of actual sensed pressure insufficient to initiate substantial reversible blocking. However with increasing plasma flow rate the increase in pressure rises in a non-linear fashion (corresponding to the regime of reversible blocking) until irreversible blocking or plugging of the filter occurs and the curve rises rapidly. Each of these fluid characteristic curves 220 pierces the control plane 102 calculated from points P and Q and offset a distance F from the prediction plane 100 at a point 0 where the rate of increase of curves 220 is more rapid than would be predicted by a linear extrapolation of the linear portion of each curve 220. FIG. 2a illustrates the fluid characteristics diagram of the same filter system as shown in FIG. 2 except that constant blood flow characteristics curves 220 have been replaced by constant plasma flow characteristics curves 230. For ease of understanding the figure numerals in FIG. 2a are the same as those of FIG. 2. Each curve 230 lies along a plane (not shown) orthogonal to a plane of constant pressure and parallel to the feed flow axis. The linear portion of each curve 230 also lies along the prediction plane 100 but rises therefrom in the non-linear portion to pierce control plane 102 at operating point T. Operating point T represents the minimum blood flow rate at which a required constant plasma flow can be achieved without causing irreversible blocking or plugging of the filter.

Thus by adjusting the actual blood flow and plasma flow rates to correspond to those on the control plane 102 associated with either a point 0 for substantially maximum plasma flow or a point T for substantially minimum blood flow as represented in the three dimensional coordinate space of FIG. 2 or FIG. 2a, the filter will never experience excessive undesirable plugging.

Translation of the prediction plane 100 upward by an experimentally determined pressure offset (i.e., 12 mm Hg) results in control plane 102 intersecting all possible fluid characteristic curve(s) 220 or 230 at an operating point above the prediction plane 100 where reversible blocking has begun to occur but irreversible blocking or plugging of the membrane pores is not taking place. If the pressure offset translation magnitude between the prediction plane 100 and control plane 102 is made too great, the operating point will occur at a point having too high a TMP and irreversible blocking or plugging of the filter membrane 32 will begin to occur. As this plugging proceeds over time the effective membrane area will decrease from the initial area of 40 square centimeters and the slope of the fluid characteristics curves 220 or 230 will increase. Hence, with reference to FIG. 2, the operating point 0 will begin to move toward lower plasma flow rates and down the fluid characteristics curve 220 toward the zero plasma flow rate axis. However, so long as the offset is chosen to enable the control plane 102 to intersect the fluid characteristic curve 220 at an operating point below the pressure and filtrate flow rate at which irreversible blocking or plugging begins to occur, stable operation of the filter system 12 may be obtained at a relatively high filtrate flow rate, maximized by the measurement of the pressure-flow characteristics of the instant filter device and the instant feed fluid characteristics.

In general, since the control plane 102 is mathematically determined in response to the actual sensed operating point Q, or points P and Q, the feed flow rate slope and the filtrate flow rate slope of the control plane 102 can be varied relative to the prediction plane 100 to improve operating conditions which may depend upon the particular application and filtering configuration of the filter system 12. It will be appreciated that depending upon the particular fluid characteristics and filter system characteristics, other adaptive control curve shapes might be utilized to optimize operation of the adaptive control system 10.

Control plane 102 with zero flow intercept P(control) as defined above is described by a control function that is not a simple linear function dependent upon a single variable. Rather it contains terms that are dependent upon feed flow (blood flow in the preferred embodiment) and upon filtrate flow (plasma flow in the preferred embodiment). The equation for the control function of the improved filter system is expressed as follows:

$$P2 = TMP + P(spin) + P(gravity) + P(blood\ flow) + P(atmos)$$

wherein the terms in P2 are as defined above.

Figure 4:
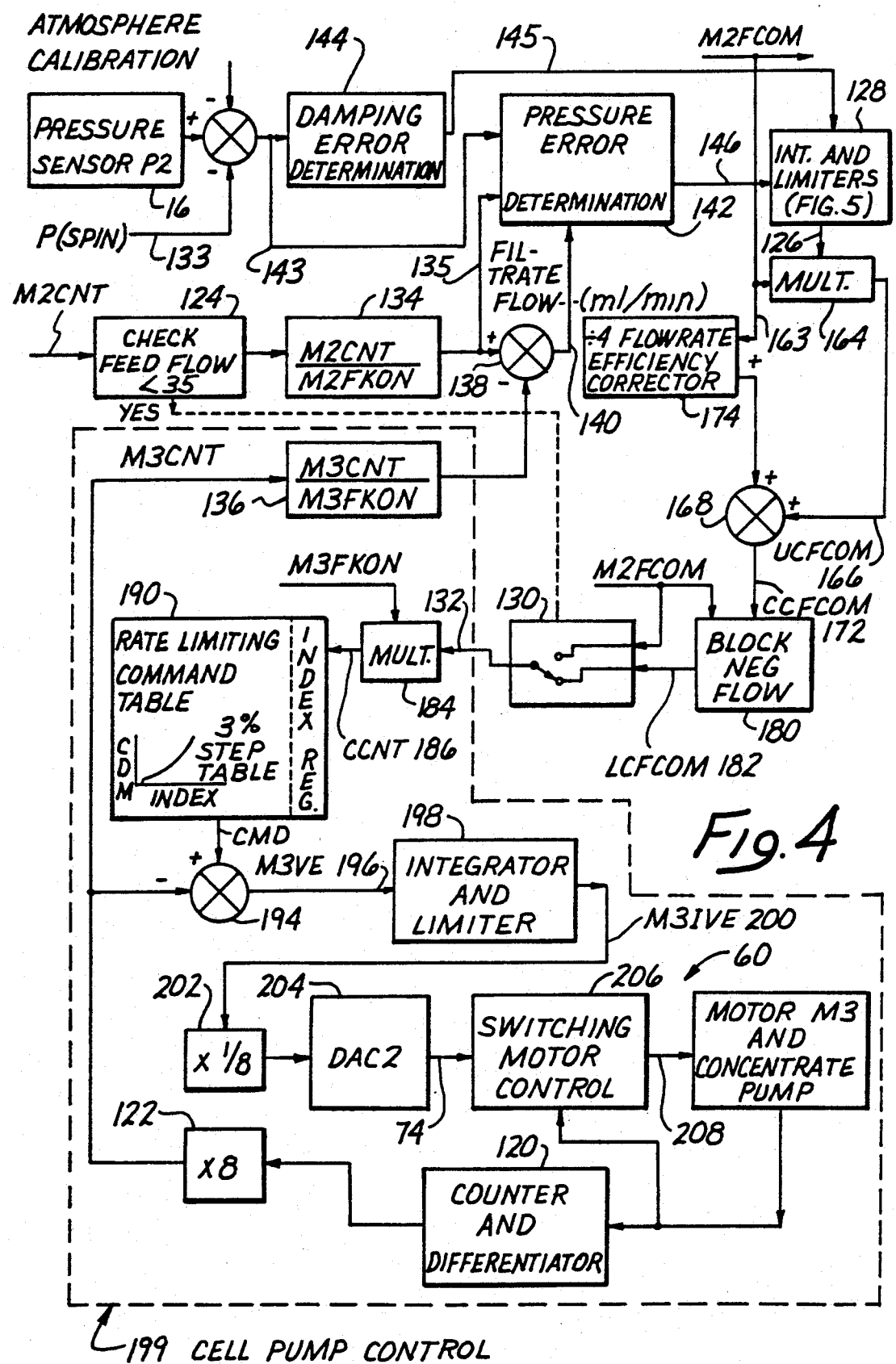
FIG. 4 is a detailed block diagram and schematic representation of a repetitive motor control update cycle for commanded blood flow shown generally in FIG. 3.

The operating sequence of the adaptive filter fluid flow control system 18 is illustrated in FIG. 4, to which reference is now made. As noted previously, the filter fluid flow control system 18 comprises a data processor which performs all data processing activities for the plasmapheresis system of which the adaptive filter flow control system 10 is a portion. The control system 18 controls the velocity of all motors in the plasmapheresis system including filter motor 44, motor M2 for peristaltic feed pump 58, and motor M3 for peristaltic concentrate pump 60. Normal processor operations are interrupted every 50 milliseconds to update motor velocity commands. During a typical motor control update cycle the processor detects and stores all of the feedback data, including positional and time information from the motors 44, 58 and 60 and pressure information over line 86 from P2 pressure sensor 16. The processor then updates the velocity commands for the filter motor 44, motor M2 for peristaltic feed pump 58 and then motor M3 for peristaltic concentrate pump 60.

While in general the peristaltic feed pump 58 could be utilized to control the rate of concentrate flow from filter system 12, in the present application it is desired to control the peristaltic feed pump 58 in response to an availability of feed fluid and adapt the pumping rate of peristaltic concentrate pump 60 to changes in the feed fluid flow rate to maintain a desired concentrate flow rate. Other implementations of the concepts of this invention involve the use of a filtrate pump wherein the filtrate is commanded. In the present example, optimal control is thus obtained by first updating the M2 motor velocity command for peristaltic feed pump 58 so that current velocity information is available during the course of the same update cycle when motor velocity commands for motor M3 driving peristaltic concentrate pump 60 are updated.

Operation for a given filtration operation or session begins with priming of the filter system 12 and the conduit tubing connecting the filter system 12 to the pumps 58, 60 and to filtrate container 22. This priming operation is conducted a relatively low, constant flow rates which are experimentally predetermined to be well within the flow capabilities of the system. For example, the peristaltic feed pump 58 may be operated at a flow rate of 60 milliliters per minute while the peristaltic concentrate pump 60 is operated at a flow rate of 40 milliliters per minute which accordingly results in a concentrate flow rate of 20 milliliters per minute (40% of the feed fluid flow rate) through filter system 12 and into container 22. The priming operation stabilized system operating conditions and particularly the pressure head which becomes a constant and contributes to the 0 flow rate axis intercept of the prediction plane 100 (FIGS. 2 and 2a).

After priming has stabilized system operating points, the next executed step is to obtain actual operating curve data. During this operating step actual operating point data is sensed such as the pressure point Q at a filtrate flow rate of 20 milliliters per minute and sufficient additional operating point data is recorded to determine the values of the blood flow slope and the plasma flow slope. Typical sensed pressure might be 79 mm Hg at 5 milliliters per minute and 88 mm Hg at 20 milliliters per minute. When the control plane 102 is mathematically derived from these two points the plasma flow slope has a value of (Pressure Q-Pressure P) mm Hg/(20-5) ml/minute. The blood flow slope can be similarly calculated using actual pressure readings at two blood flow rates. In some cases this slope may be substantially consistent from donation to donation. In this case only a single point, such as point Q may be required, using a predetermined plasma flow slope of 10 mm Hg/20 ml/min and a predetermined blood flow slope of 8 mm Hg/30 ml/min, for example.

In practice it has been found advantageous to use as a sensed actual operating point Q the average of a plurality of different data samples. The averaging of a plurality of samples tends to smooth out the substantial pressure pulses which are induced by the peristaltic feed pump 58 and to compensate for a relatively low resolution of the P2 pressure sensor 16. While higher quality pressure sensors and date converters are of course available, for the present application it has been found that the best pressure sensor and data converter which is economically suitable has a resolution of only 4 mm Hg in the least significant bit. By using as the final pressure value at a given operating point; an average of 4 or 5 or more samples, the effective resolution of the P2 pressure sensor 16 can be increased to about 1.5 mm Hg.

After actual operating point data has been obtained at 1 or more points such as point P and Q in FIG. 2, the control system 18 determines the control plane 102. As indicated previously, the control plane 102 may be generated by simply translating prediction plane 100 upward or downwards by a fixed pressure offset value, such as +12 mm Hg as in the present example. Alternative derivations may be utilized as well, depending upon the particular application.

It is desirable to use point P and Q to calculate the prediction plane 100 from the control function to accurately reflect the actual characteristics of the feed fluid, the pump flow constants, and the filter configuration. Since the plasma flow and blood flow slopes and thus the extrapolated control plane 102 are generated from relative pump command flow rates, scale errors between pump command flow rates and actual flow rates are eliminated if two or more calibration points are used.

However, in the present example it has been found to be economically expedient to use only a single actual operating point which has been selected to be point Q. Experiments have shown that for the specific application of filtering plasma from whole blood, the slopes of the prediction plane 100 and hence of the control plane 102 remain fairly uniform at the above suggested values from session to session notwithstanding substantial changes in the hematocrit dependent viscosity of the whole blood feed fluid. At the same time, the resolution of the P2 pressure sensor 16 is relatively coarse compared to the 12 mm Hg per 20 milliliters per minute plasma flow rate slope of the linear prediction plane 100. As a result of these factors, it has been found advantageous for the specific application of a plasmapheresis system to use the above experimentally predetermined plasma flow and blood flow slopes in calculating the prediction plane 100 and position it at the pressure point Q actually sensed at the filtrate flow rate of 10 milliliters per minute. The control plane 102 is then determined as having a 12 mm Hg offset from this prediction plane 100 and thus has predetermined slopes and vertical position (pressure offset value) determined from actual sensed operating point data.

Once the control plane 102 is established, the system proceeds to execute motor control update cycles 20 times per second until the filtration process is complete. When filtration is complete the motor M3 driving concentrate pump 60 is stopped along with other motors in the plasmapheresis system.

Figure 5:
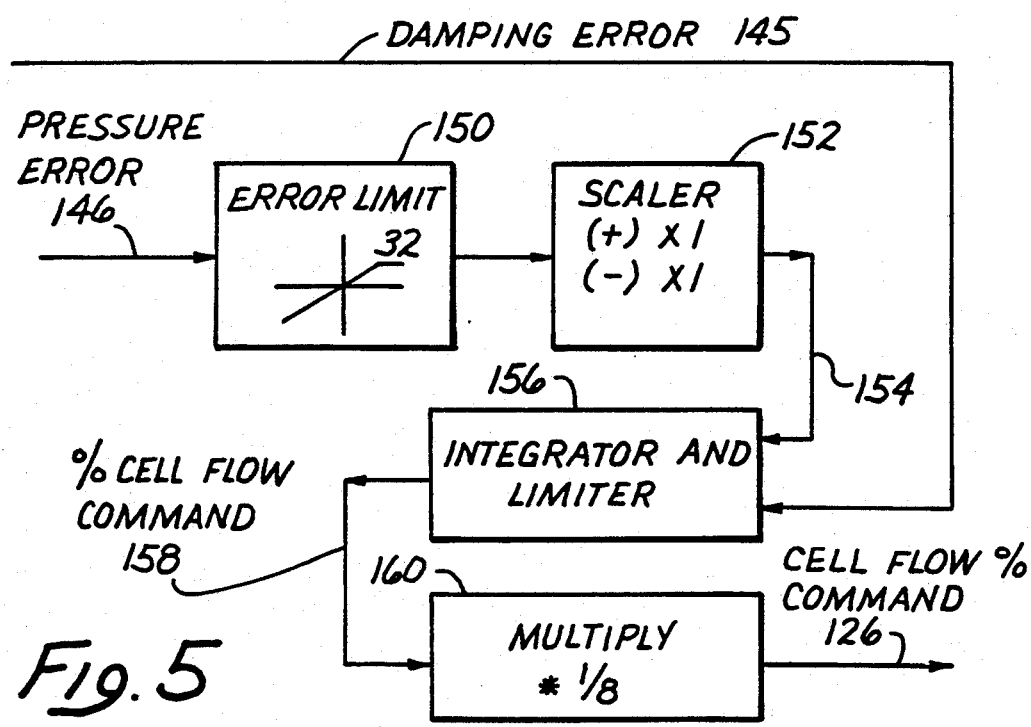
FIG. 5 is a detailed block diagram representation of a portion of the motor control update cycle for commanded blood flow shown in FIG. 4.

The servo control used in updating the velocity of the motor M3 driving the concentrate pump 60 is illustrated in greater detail in FIG. 5, to which reference is now made. It should be appreciated that while FIG. 5 illustrates the velocity update cycle for motor M3 in block diagram and schematic form, the mathematical and conditional operations represented by the various blocks are actually executed by the data processor comprising filter fluid flow control system 18. As indicated previously, the velocity control update cycle begins with sensing of all system conditions and calculation of actual feedback motor velocities. The updating of motor velocity for motor M3 is typical of the procedure for all motors in the system and is executed at a counter and differentiator step 120. Employed by this step is a hardware counter which is incremented by each feedback pulse from motor M3. This counter is thus a positional reference indicating 12 times the number of revolutions of motor M3. This position count is in effect differentiated to produce a velocity signal by subtracting the position count for the previous update cycle from the present position count. The current position count is then stored for use in the next update cycle. The current velocity count is then scaled by multiplying it by eight at a step 122 to produce a motor M3 count signal M3CNT. In similar fashion a motor 2 count signal M2CNT is determined for the motor M2 for feed pump 58.

At step 124 the velocity signal M2CNT is checked to see if the motor M2 has reached a velocity corresponding to a feed flow rate of 35 ml/min, for example (lower values would be required for situations of low teed flow source capacity). If yes, normal operation is assumed and a full update cycle is executed. However, if the detected feed flow velocity is less than 35 ml/min, a special case (such as at startup) or other abnormal operating condition is presumed and the concentrate pump 60 is constrained to match the flow rate of the feed fluid pump 58 so that a filtrate flow rate of 0 is produced. This is accomplished by arbitrarily setting a concentrate or cell flow percent command 126 output from an integrator and comparator step 128 to a value representing 100%. As will be apparent from a more detailed description below, this corresponds to a filtrate or plasma flow rate of 0 and precludes undesirable transients in the servo loop once the feed fluid or whole blood flow rate exceeds 35 ml/min and the filtrate flow rate is then permitted to ramp up from 0 to a steady state flow rate. As the integrator and comparator is set to output the 100% value a virtual switch 130 is set to produce as M3 velocity command output 132 the previously updated feed pump motor M2 flow command, M2FCOM163. This effectively commands the motor M3 to follow the velocity of motor M2.

Under normal circumstances the feed fluid flow will be greater than 35 ml/min, so that the system then proceeds to divide signal M2CNT by a flow constant M2FCON at a step 134 and divide signal M3CNT by a motor 3 flow constant M3FCON at a step 136. These division steps 134, 136 merely provide a unit conversion from the raw motor count units to a flow rate of milliliters per minute utilized in the servo control loop. A subtractor 138 subtracts the concentrate flow rate 137 from the feed fluid flow rate 135 to produce a filtrate fluid flow rate signal 140 at the output thereof. This filtrate flow signal 140 becomes one input to a pressure error and determination step 142. Pressure error and limit determination step 142 also receives as a second input an atmospheric and P(spin) compensated pressure signal 143, which is obtained by receiving a current actual pressure indication from P2 pressure sensor 26, and calibrating the pressure signal by subtracting actual atmospheric pressure, and P(spin) 133. Time sampling as commonly utilized in computer control systems using analog to digital converters may be employed.

The damping error determination step 144 uses conventional second-order filtering methods to provide loop compensation for stability of operation.

Figure 3:
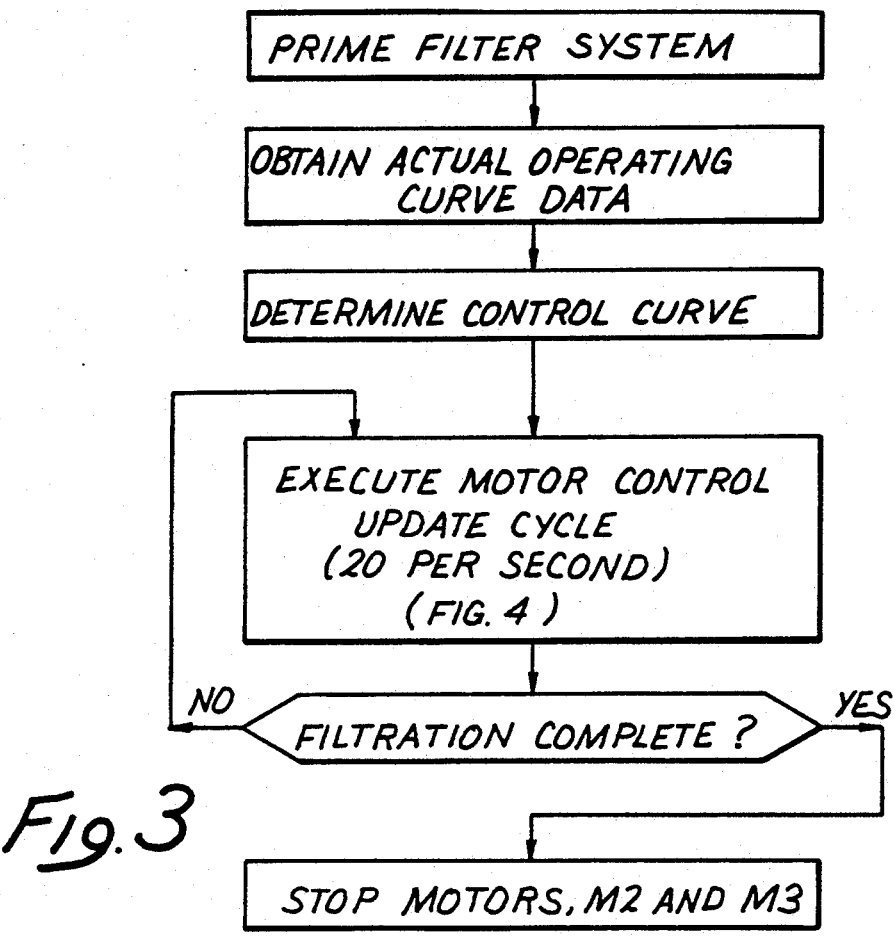
FIG. 3 is a flow chart illustrating a control sequence for the filter system shown in FIG. 1.

Within pressure error and limit determination step 142 the filtrate flow signal 140 is utilized to access the control plane 102 (FIGS. 2 and 3). The value on control plane 102 at the indicated filtrate flow rate and blood flow rate is calculated and if this value is less than or more than the compensated actual pressure value represented by signal P2LEDLAG, then signal P2LED-LAG is subtracted from the calculated value to produce a pressure error signal 146. The pressure error signal 146 and damping error signal 145 are integrated and compensated at a step 128 which is shown in greater detail in FIG. 5 to which reference is now made.

Referring now to FIG. 5, the pressure error signal 146 is subjected to an error limit step 150 at which a positive upper limit of 32 mm Hg is placed upon the pressure error signal 146. The limited pressure error signal is then subject to a scaler step 152 at which separate paths are available to multiply positive or negative pressure error signals by a constant. In the present application the constant has a value of "one" for both positive and negative values but the mechanism is made available to permit different scaling for positive and negative values where a particular application might make separate scaling desirable. The scaler 152 can conceptually be thought of as providing a change of units of measurement and outputs a signal 154 which is effectively a percent concentrate flow error signal.

Damping error signal 145 is provided to the integrator and limiter 156 to achieve stability. Integrator and limiter 156 receives the percent cell flow error signal 154 and the damping error signal 145, performs a sign change, integrates the error signals to produce a percent cell flow command signal 158 and imposes upon the percent cell flow command signal 158 an upper limit equal to a constant P2RSHLIM and lower limit equal to a constant P2RSLLIM. In the present application the upper limit P2RSHLIM has a value corresponding to a packed cell or concentrate flow rate of 100 percent of the feed fluid flow or 0 percent filtrate flow rate. Similarly, the lower limit has a value which corresponds to a concentrate flow rate of approximately 37 percent of the feed fluid flow rate or a filtrate flow rate of approximately 63 percent of the feed fluid flow rate. This lower limit on the percent cell flow command 158 in effect operates as a safety feature preventing excess filtrate flow through a filter.

Referring back to FIG. 4, the cell flow percent command 126 is communicated to a multiplier 164 which multiplies the cell flow percent command 126 times the commanded feed flow motor velocity command M2FCOM163 and simultaneously performs a scaling function by dividing the product by 256. Output of multiplier 164 is thus an uncompensated concentrate flow command 166 commanding concentrate flow in units of milliliters per minute.

The uncompensated flow command 166 is communicated to an adder 168 where it is added to a compensation signal 170 to produce a compensated cell flow command, CCFCOM 172.

A filtrate flow rate efficiency corrector 174 receives the commanded motor 2 velocity signal, M2FCOM, divides it by 4, and presents the result to an adder 176. The efficiency correction dynamically feeds forward a correction to substantially compensate any known filter efficiency variations as a function of blood flow and plasma flow rates by adjusting the cell flow rate. For example, at a feed fluid flow rate of 60 ml per min a typical stabilized operating point might permit a yield of 80% of available plasma. If the available plasma is 60% of the feed flow rate, then the plasma or filtrate flow rate will be 49% of the feed fluid flow rate or 28.8 ml per minute. As the feed fluid flow rate increases to 100 ml per min (for example), the operating point may stabilize with filtrate being only 70% of the available flow rate. This would reduce the stabilized filtrate flow rate to 42.0 mil per min.

However, if the control system follows a rapid change in feed fluid flow rate from 60 to 100 ml per min with a constant percentage filtrate flow rate, the instantaneous filtrate flow rate will be 48.0 mil per minute. This will produce a pressure error signal which will gradually reduce the filtrate flow rate to the stable 42.0 ml per min operating point. However, in the meantime the filter 32 may be experiencing irreversible blocking or plugging. The feed forward of the feed fluid command signal M2FCOM through flow rate efficiency corrector 174 enables the motor control system to more quickly adjust to changes in feed fluid flow rates and thus reduce or eliminate periods during which the filter 32 experiences reversible blocking.

The compensated flow command 172 is communicated to a block negative flow step 180 where checks are made to assure that neither concentrate fluid nor filtrate fluid have a negative flow. Negative flow of concentrate fluid is blocked by limiting the compensated concentrate flow command 172 to a value greater than or equal to 0. Negative filtrate flow is prevented by limiting the compensated concentrate flow command signal 172 to values less than or equal to the feed flow motor velocity command signal, M2FCOM. The block negative flow step 180 outputs a limited concentrate flow command signal 182 to the virtual switch step 130. It will be recalled that step 130 typically applies the limited concentrate flow command signal 182 to the multiplier 184. However, in the event that feed flow is less than a predetermined minimum of 35 ml/min, virtual switch 130 substitutes the feed motor flow command M2FCOM for the M3 velocity command signal 132 which is applied to the multiplier 184 located within the indicated cell pump control 199.

Multiplier 184 performs a scaling function to convert from milliliters per minute to flow velocity in terms of Hall device feedback counts per update cycle. Multiplier 184 multiplies the M3 velocity command signal 132 by a motor flow constant M3FKON which relates the output concentrate count command signal 186 to the M3 velocity command 132.

The concentrate count command 186 is presented to an exponential rate limiting command table 190. Rate limiting command table 190 imposes a slew rate limit upon the change of fluid flow velocity produced by the peristaltic concentrate pump 60. In effect, the concentrate flow rate is permitted to increase at a rate of only 3% per update interval but may be rapidly decelerated. Although not specifically shown, the feed flow peristaltic pump 58 is similarly limited to flow acceleration rates of 3% per update time interval. Consequently, during transient acceleration conditions, the concentrate flow is maintained as a substantially constant percent of feed flow as the two pumps 58, 60 are being accelerated, both limited to 3% change per update cycle.

The rate limiting command table is implemented as a stored look up table storing the command values which form the output motor 3 commanded count signal, M3CCNT. These values are addressed by an index value stored in an index register within rate limiting command table 190 (physically within a data store age location in filter fluid flow control system 18). At an index value of 0 the stored command value is 0 to assure a commanded 0 velocity for the peristaltic concentrate pump 60. At an index value of 1 the command value, CMD, has an experimentally predetermined value selected to overcome system offsets and friction forces to provide the minimum value which will sustain rotation of motor M3 driving peristaltic concentrate pump 60. Thereafter, the command value, CMD, is increased by three percent for each unity increment in the index address value.

As a further limit upon the acceleration of the peristaltic concentrate pump 60, the value accessed by the current index is compared to the concentrate count signal 186 during each update cycle. If the concentrate count signal 186 is less than the value accessed by the current index, the command value, CMD, is set to the concentrate count signal ICCNT 186. On the other hand, if the concentrate count signal 186 is greater than the stored table value accessed by the current index, the index value is incremented by 1. After a sufficient number of update cycles a steady state condition will be reached wherein the index value stored in the index register accesses a tabulated command value equal to or slightly greater than the concentrate count signal 186.

The actual M3 motor count signal, M3CNT is subtracted from the velocity command signal, M3CCNT, at a subtractor step 194 to generate a motor M3 velocity error signal, M3VE 196. The velocity error signal 196 is then integrated at an integrator and limiter step 198 to produce an integrated velocity error signal, M3IVE 200. Integrator and limiter 198 imposes an upper limit representing 100 ml/min upon the integrated velocity error signal, M3IVE 200.

Integrated velocity error signal 200 is then scaled by multiplication by $\frac{1}{8}$ at a multiplier 202 and then communicated to a digital-to-analog converter 204 designated DAC2. Digital-to-analog converter 204 is an actual hardware device which is represented as being contained within the filter fluid flow control system 18 in FIG. 1. The analog output from DAC2 204 is communicated to a switching motor control system 206 over line 74. Switching motor control system 206 is represented as being part of peristaltic concentrate pump 60 in FIG. 1 and converts the analog velocity command received over line 74 to a switched energizing pulse 208 which actually energizes motor M3 which in turn rotates the concentrate pump.

Referring again to FIG. 4, the motor control update cycle is periodically executed 20 times per second until a filtration subcycle has been completed. After completion of the filtration subcycle the feed fluid motor M2 and the concentrate fluid motor M3 are both commanded to stop and execution of the update cycle is terminated.

Figure 6:
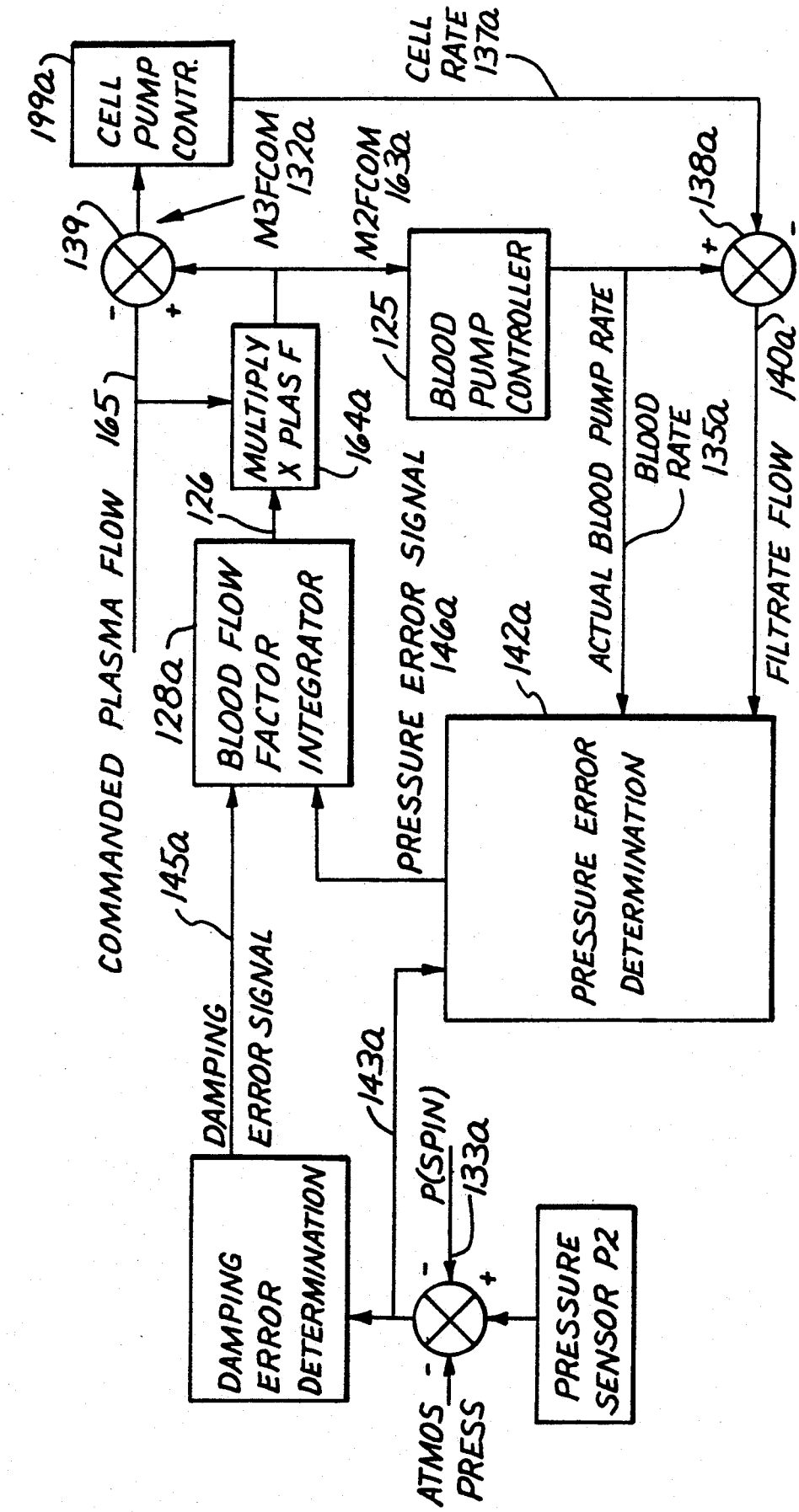
FIG. 6 is a functional block diagram and schematic representation of a repetitive motor control update cycle for commanded plasma flow shown in FIG. 4.

Referring now to FIG. 6, a simplified functional block diagram and schematic is shown to illustrate a method of control for a constant filtrate flow wherein feed flow rate (blood rate) 135a is minimized in response to a commanded filtrate flow rate (plasma) 165 through the application of this invention.

Individual functional elements of FIG. 6 labeled with the letter "a" suffix correspond to like functional elements of FIG. 4 similarly numbered. Such similarly numbered elements perform substantially similar functions in the two control systems.

Filtrate flow 165 is subtracted from feed flow command (M2FCOM)163a in subtractor 138, providing concentrate cell flow command (M3FCOM) 132a which is provided to cell pump control 199a. The cell rate 137a is subtracted from blood rate 135a (from blood pump controller 125) in subtractor 138a and provides a filtrate flow signal 140a to the pressure error determination function 142a.

Blood flow factor integrator 128a serves a similar function as the integrator/limiter 128 of FIG. 4, with similar inputs damping error signal 145a and pressure error signal 146a as more thoroughly described in reference to FIG. 4.

The cell pump control 199a and the blood pump control 125 then work in concert with the filter 40 of FIG. 1 as described above to provide a constant output filtrate flow in response to the filtrate flow command 165 while substantially minimizing blood flow 135a.

While there have been shown and described above particular arrangements of adaptive filter fluid flow control systems in accordance with the invention for the purpose of enabling a person of ordinary skill in the art to make and use the invention, it will be appreciated that the invention is not limited thereto. For instance, one skilled in the art will appreciate that a three dimensional space with a control plane and fluid characteristic curves representing pressure at various commanded rates of constant concentrate flow could be constructed to optimize filter operations for minimum blood flow and/or maximum filtrate flow. Accordingly, any modifications, variations, or equivalent arrangements within the scope of the attached claims should be considered to be within the scope of the invention.

What is claimed is:

1. A fluid flow control system for controlling a flow of filtrate through a filter system having a filter membrane with a predictable transmembrane pressure-filtrate flow rate-feed flow rate relationship when the filter system is operated under nonobstructing operating conditions, the control system comprising:
   means for substantially precluding irreversible blocking of said filter membrane including,
   a flow regulating system coupled to control flows of feed fluid, concentrate fluid and filtrate fluid in the filter system in response to at least one control signal;
   a pressure sensor disposed to sense and generate indications of transmembrane pressure in the filter system; and
   means for maintaining the transmembrane pressure at an operating point lying upon a particular three dimensional control surface having a shape conforming to the predictable transmembrane pressure-filtrate flow rate-feed flow rate relationship, and a pressure offset from the received pressure indication by a selected pressure difference.

2. The fluid flow control system according to claim 1 above, wherein the predictable transmembrane pressure-filtrate and transmembrane pressure-feed flow rate relationships are substantially linear so that pressure increases with filtrate and feed flow rates.

3. The fluid flow control system according to claim 2 above, wherein the fluid flow control system is operable to determine an actual nonobstructing transmembrane pressure-operating point during each filtration cycle and to determine the predictable transmembrane pressure-filtrate flow rate-feed flow rate relationship as a plane passing through the determined actual operating point and having a first slope reflecting the feed flow versus pressure fluid characteristics of the system and a second slope reflecting the filtrate flow versus pressure fluid characteristic of the system.

4. The fluid flow control system according to claim 2 above, wherein the fluid flow control system is operable to determine a plurality of actual nonobstructing transmembrane pressure operating points dependent upon actual feed fluid, fluid pumping system, and filter membrane characteristics encountered during each filtration cycle and determine the predictable transmembrane pressure-filtrate flow-feed flow relationship as a plane passing through the determined actual operating points.

5. The fluid flow control system according to claim 1 above, wherein the fluid flow control system is operable to collect data defining an actual nonobstructing transmembrane pressure operating point during each filtration cycle and to determine the particular control surface in response to the collected actual operating point data.

6. The fluid flow control system according to claim 5 above, wherein the first and second slopes are different and the pressure offset is empirically derived and reflects the physical characteristics of the filter system and the feed fluid.

7. The fluid flow control system according to claim 1 above, wherein the fluid flow control system is operable to determine a plurality of actual nonobstructing transmembrane pressure operating points dependent upon actual feed fluid, fluid pumping system, and filter membrane characteristics encountered during each filtration cycle and to determine the particular control surface in response to the determined actual operating points.

8. The fluid flow control system according to claim 1 above, wherein the flow regulating system includes a concentrate pump coupled to pump concentrate fluid from the filter system and the at least one control signal from the fluid flow control system controls the pumping system by controlling the flow rate of the concentrate pump.

9. The fluid flow control system according to claim 1 above, wherein the flow regulating system includes a feed fluid pump operating to pump feed fluid to the filter system and a concentrate pump coupled to pump concentrate fluid from the filter system and wherein the at least one control signal from the fluid flow control system controls the pumping system by controlling the flow rate of the concentrate pump relative to the flow rate of the feed fluid pump.

10. The fluid flow control system according to claim 1 above, wherein the flow regulating system includes a feed fluid pump operating to pump feed fluid to the filter system and a filtrate pump coupled to pump filtrate fluid from the filter system and wherein the at least one control signal from the fluid flow control system controls the pumping system by controlling the flow rate of the filtrate pump relative to the flow rate of the feed fluid pump.

11. The fluid flow control system according to claim 1 above, wherein the flow regulating system includes a feed fluid pump operating to pump feed fluid to the filter system and a filtrate pump coupled to pump filtrate fluid from the filter system and wherein the at least one control signal from the fluid flow control system controls the pumping system by controlling the flow rate of the feed pump relative to the flow rate of the filtrate fluid pump.

12. A fluid flow control system comprising:
means for substantially precluding irreversible blocking of said filter membrane including,
a filter system having a filter membrane with a predictable transmembrane pressure-filtrate flow rate-feed flow rate relationship when the filter system is operated under nonobstructing operating conditions;
a flow regulating system coupled to control flows of feed fluid, concentrate fluid and filtrate fluid in the filter system;
a pressure sensor disposed to sense and generate indications of transmembrane pressure in the filter system; and
means for maintaining transmembrane pressure at an operating point lying upon a particular three dimensional control surface having a shape conforming to the predictable transmembrane pressure-filtrate flow rate-feed flow rate relationship and a pressure offset from the indicated transmembrane pressure by a selected pressure difference.

13. A filter fluid flow control system comprising:
means for substantially precluding irreversible blocking of said filter, including,
means for filtering coupled to receive and filter a feed fluid, the filtering means including a porous separator separating filtrate fluid from the feed fluid to produce concentrate fluid, the flow of filtrate fluid through the membrane having a predictable pressure surface characteristic for nonobstructing filtering conditions;
means for pumping disposed to control the flow of feed fluid, concentrate fluid and filtrate fluid in the filtering means;
means for sensing the indicating pressure differential across the separator; and
means for maintaining the pressure across the separator and filtrate fluid flow rate at a point lying upon a flow control surface having a shape conforming to the predictable pressure surface characteristic and a pressure offset relative to at least one nonobstructing filter condition actual system operating point.

14. The filter fluid control system according to claim 13 above, wherein the feed fluid is blood, the concentrate is packed cells, and the filtrate is plasma, and wherein the flow rate of plasma is controlled relative to the flow rate of blood and wherein the pressure offset is empirically derived and reflects the physical characteristics of the filter system and of the blood.

15. The filter fluid control system according to claim 13 above, wherein the porous separator is a rotating membrane and the filtrate has a centripetal flow direction through the rotating membrane.

16. A filter fluid flow control system comprising:
means for substantially precluding irreversible blocking of said filter membrane including,
means for filtering coupled to receive and filter a feed fluid, the filtering means including a porous separator separating filtrate fluid from the feed fluid to produce concentrate fluid, the flow of filtrate fluid through the membrane having a predictable three dimensional pressure-filtrate flow rate-feed flow rate surface characteristic for nonobstructing filtering conditions;
means for pumping disposed to control the flow of feed fluid, concentrate fluid and filtrate fluid in the filtering means;
means for sensing and indicating pressure differential across the separator; and
means for maintaining the pressure across the separator and feed fluid flow rate at a point lying upon a flow control surface having a shape conforming to the predictable surface characteristic and a selected pressure offset relative to at least one nonobstructing filter condition actual system operating point.

17. The filter fluid control system according to claim 16 above, wherein the feed fluid is blood, the concentrate is packed cells, and the filtrate is plasma, and wherein the flow rate of plasma is controlled relative to the flow rate of blood and wherein the pressure offset is selected to locate the system operating point in the regime of reversible filter blocking.

18. The filter fluid control system according to claim 16 above, wherein the porous separator is a rotating membrane and the filtrate has a centrifugal flow direction through the rotating membrane.

19. The method of optimizing a flow of filtrate through a filter comprising the steps of:
providing means for substantially precluding irreversible blocking of said filter by,
determining a three dimensional flow rate control surface in a three dimensional filtrate flow rate versus transmembrane pressure versus feed flow rate coordinate system, the control surface having a shape conforming to sensed nonobstructing concentrate flow rate versus transmembrane pressure characteristic and a predetermined pressure offset;
determining said value; and
controlling the filter operating point to produce filter operation at a point which lies upon the flow rate control surface.

20. A method of optimizing flow of filtrate through a filter comprising the steps of:
providing means for substantially precluding irreversible blocking of said filter by,
determining a three dimensional flow rate control surface in a filtrate flow rate versus transmembrane pressure versus feed flow rate coordinate system, the control surface having a shape conforming to a sensed nonobstructing transmembrane pressure characteristic and a selected pressure offset, the control surface being determined by detecting at least one nonobstructing actual filter operating point and using as the know nonobstructing transmembrane pressure characteristic a three dimensional prediction surface passing through the detected at least one nonobstructing actual filter operating point;
determining said value; and
automatically controlling the filter operating point to produce filter operation at a point which lies upon the flow rate control surface.

21. The method according to claim 20 above, wherein the prediction surface is a plane in the three dimensional coordinate system.

22. The method according to claim 20 above, wherein the detecting step detects exactly one nonobstructing actual filter operating point and the prediction plane has a first slopes reflecting the feed flow versus pressure fluid characteristic of the system and a second slope reflecting the filtrate flow versus pressure fluid characteristic of the system.

23. The method according to claim 20 above, wherein the detecting step detects exactly two nonobstructing actual filter operating points and the prediction surface is a plane and passes through the two detected nonobstructing actual filter operating points.

24. The filter system according to claim 20 above, wherein the pumping system includes a feed fluid pump pumping the feed fluid and wherein the fluid flow control system operates to command operation of the feed fluid pump at a commanded feed fluid velocity and to further control the operation of the pumping system to tend to reduce the pressure difference in response to a product of the integral of the pressure difference and the commanded feed fluid velocity.

25. The filter system according to claim 24 above, wherein the pumping system includes a flow rate efficiency correction to further maximize the safe operating filtrate flow rate.

26. The filter system according to claim 25 above, wherein the feed is blood and the filtrate is plasma.

27. An adaptive flow filter system comprising:
a filter receiving a flow of feed fluid and separating the received feed fluid to produce separate flows of concentrate fluid and filtrate fluid;
means for substantially precluding irreversible blocking of said filter including,
a pumping system coupled to cause the feed fluid, concentrate fluid and filtrate fluid to flow at controlled flow rates;
a pressure sensor coupled to sense and indicate any pressure differential between the received feed fluid and filtrate fluid; and
means for controlling said pumping system operable in a three dimensional pressure versus feed fluid flow rate versus filtrate flow rate coordinate system to determine at lest one filter system actual operating point and to determine from the at least one actual operating point a control surface having a pressure offset relative to a locus of anticipated nonblocking actual operating points, said means for controlling said pumping system being operable to control the pumping system in response to a pressure difference as indicated by the pressure sensor between an actual sensed pressure at an operating point having known feed and filtrate flow rates and a pressure at a point on the control curve having corresponding feed and filtrate flow rates to tend to reduce the pressure difference, these relationships being scaled linearly with feed fluid flow rates.

28. The filter system according to claim 27 above wherein the fluid flow control system operates to integrate the pressure difference and control the pumping system in response to the integral of the pressure difference.

29. An adaptive flow filter system comprising:
a filter receiving a flow of feed fluid and separating the received feed fluid to produce separate flows of concentrate fluid and filtrate fluid;
means for substantially precluding irreversible blocking of said filter including,
a pumping system coupled to cause the feed fluid, concentrate fluid and filtrate fluid to flow at controlled flow rates;
a pressure sensor coupled to sense and indicate any pressure differential between the received feed fluid and filtrate fluid; and
means for controlling said pumping system operable in a three dimensional pressure versus feed fluid flow rate versus filtrate flow rate coordinate system to determine at least one filter system actual operating point and to determine from the at least one actual operating point a control surface having a pressure offset relative to a locus of anticipated nonblocking actual operating points, said means for controlling said pumping system being operable to control the pumping system in response to a pressure difference as indicated by the pressure sensor between an actual sensed pressure at an operating point having known feed and filtrate flow rates and a pressure at a point on the control curve having corresponding feed and filtrate flow rates to tend to reduce the pressure difference, these relationships being scaled linearly with filtrate fluid flow rates.

30. The filter system according to claim 29 above wherein the fluid flow control system operates to integrate the pressure difference and control the pumping system in response to the integral of the pressure difference.

31. The filter system according to claim 30 above, wherein the pumping system includes a filtrate fluid pump pumping the filtrate fluid and wherein the fluid flow control system operates to command operation of the filtrate fluid pump at a commanded filtrate fluid velocity and to further control the operation of the pumping system to tend to reduce the pressure difference in response to a product of the integral of the pressure difference and the commanded filtrate fluid velocity.

32. The filter system according to claim 31 above, wherein the pumping system includes a flow rate efficiency correction to further minimize the safe operating feed flow rate.

33. The filter system according to claim 32 wherein the feed is blood and the filtrate is plasma.

34. The filter system according to claim 33 wherein the filter is a spinning membrane filter.

35. A fluid flow control system for controlling a flow of filtrate through a filter system having a filter membrane with a predictable transmembrane pressure-filtrate flow rate-feed flow rate relationship when the filter system is operated under nonobstructing operating conditions, the control system comprising:
  means for substantially precluding irreversible blocking of said filter membrane including,
  a flow regulating system coupled to control flows of feed fluid, concentrate fluid and filtrate fluid in the filter system in response to at least one control signal;
  a pressure sensor disposed to sense and generate indications of transmembrane pressure in the filter system; and
  means for maintaining the transmembrane pressure at an operating point lying upon a particular three dimensional control surface having a shape conforming to the predictable transmembrane pressure-filtrate flow rate-feed minus filtrate flow rate relationships, and a pressure offset from the received pressure indication by a selected pressure difference.

* * * * *